(12) United States Patent
Van Der Westhuizen et al.

(10) Patent No.: US 8,501,970 B2
(45) Date of Patent: Aug. 6, 2013

(54) METHOD FOR THE PREPARATION OF C-4 COUPLED FLAVONOIDS, PROANTHOCYANIDINS AND ANALOGUES THEREOF

(75) Inventors: Jan Hendrik Van Der Westhuizen, Bloemfontein (ZA); Matthew Achilonu, Bloemfontein (ZA); Susanna Lucia Bonnet, Bloemfontein (ZA)

(73) Assignee: University of the Free state, Bloemfontein (ZA)

( * ) Notice: Subject to any disclaimer, the term of this patent is extended or adjusted under 35 U.S.C. 154(b) by 117 days.

(21) Appl. No.: 12/995,379

(22) PCT Filed: Jun. 5, 2009

(86) PCT No.: PCT/IB2009/052396
§ 371 (c)(1),
(2), (4) Date: Feb. 23, 2011

(87) PCT Pub. No.: WO2009/147645
PCT Pub. Date: Dec. 10, 2009

(65) Prior Publication Data
US 2011/0160467 A1    Jun. 30, 2011

(30) Foreign Application Priority Data
Jun. 6, 2008   (ZA) .................................. 2008/04953

(51) Int. Cl.
*C07D 311/62*    (2006.01)
*C07H 17/065*    (2006.01)

(52) U.S. Cl.
USPC .......................... 549/399; 549/403; 536/18.1

(58) Field of Classification Search
USPC ......................................... 549/399; 536/18.1
See application file for complete search history.

(56) References Cited

PUBLICATIONS

Saito et al, Synlett, 2004, No. 11, p. 2040-2042 (2004).*
Achilonu, M. C. et al. (2008). Synthesis of Proanthocyanidins. Part 1. The First Oxidative Formation of the Interflavanyl Bond in Procyanidins. *Organic Letters*, 10(17): 3865-3868.
Kozikowski, A. P. et al. (2003). Studies in Polyphenol Chemistry and Bioactivity. 4. Synthesis of Trimeric, Tetrameric, Pentameric, and Higher Oligomeric Epicatechin-Derived Procyanidins Having All-4(beta),8-Interflavan Connectivity and Their Inhibition of Cancer Cell Growth through Cell Cycle Arrest. *Journal of American Chemistry*, 68(5): 1641-1658.
Steynberg, P. J. et al. (1998). Oligomeric flavanoids. Part 27. Interflavanyl bond formation in procyanidins under neutral conditions. *Tetrahedron*, 54(28): 8153-8158.

* cited by examiner

*Primary Examiner* — Bernard Dentz
(74) *Attorney, Agent, or Firm* — Saliwanchik, Lloyd & Eisenschenk

(57) ABSTRACT

The invention relates to a novel process for the preparation of C-4 coupled flavonoids, proanthocyanidins and analogues thereof. According to a specific application of the invention, there is provided a method for the preparation of proanthocyanidins and proanthocyanidin analogues.

37 Claims, No Drawings

METHOD FOR THE PREPARATION OF C-4 COUPLED FLAVONOIDS, PROANTHOCYANIDINS AND ANALOGUES THEREOF

CROSS-REFERENCE TO RELATED APPLICATIONS

This application is the U.S. national stage application of International Patent Application No. PCT/IB2009/052396, filed Jun. 5, 2009, which claims priority to South African Application No. 2008/04953, filed Jun. 6, 2008, the disclosures of each of which are incorporated herein by reference in their entirety.

FIELD OF THE INVENTION

This invention relates to a novel process for the preparation of C-4 coupled flavonoids, proanthocyanidins and analogues thereof.

BACKGROUND TO THE INVENTION

Proanthocyanidins (also known as procyanidin oligomeric proanthocyanidin (OPC) or condensed tannins) are ubiquitous in plants and are important constituents of the human diet. A wide range of potentially significant biological activities including antioxidant, anti-atherosclerotic, anti-inflammatory, antitumor, antiosteoporotic, and antiviral effects have been attributed to this class of compounds.

Proanthocyanidins are dimers, trimers, oligomers or polymers of flavanols. Flavanols (also referred to as flavan-3-ols) are a class of flavonoids and include (+)-catechin (compound 1) of Formula (A) and (−)-epicatechin (compound 2) of Formula (A). Compound 1 or compound 2, as monomer units, are linked via their 4- and 8-, or 4- and 6-positions to form proanthocyanidins. Progress in the chemistry and biology of these compounds has been slow due to the difficulty of isolating and synthesizing pure free phenolic compounds.

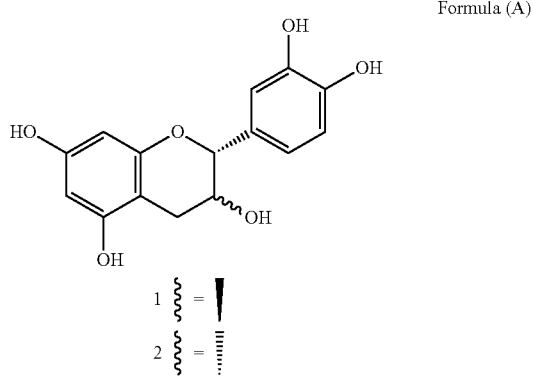

Formula (A)

The production of proanthocyanidins and analogues thereof by the introduction of flavanyl, flavonoid and other phenolic moieties at C-4 of flavan-3,4-diols is known in the art and has been achieved by acid catalyzed condensation of the appropriate nucleophilic and electrophilic units. These initial stereoselective synthetic methods played an important role in the structure elucidation of the economically important profisetinidins and prorobinetinidins from *Acacia mearnsii* (Black Wattle) and *Schinopsis* spp up to the tetrameric level.

However, the above methods were hampered by the laborious extraction procedures required to obtain optically active starting materials that occur in low concentrations in plant material. Synthetic access to proanthocyanidin dimers, trimers, tetramers, higher oligomers and polymers as well as analogues thereof has been greatly enhanced by the introduction of a C-4 leaving group for purposes of increasing electrophilicity at the C-4 benzylic position of commercially available (+)-catechin (compound 1) and (−)-epicatechin (compound 2). The introduction of a C-4 leaving group thus requires the performance of an extra step in the synthesis, namely the preparation of what will herein be referred to as C-4 functionalised precursors. Further disadvantages associated therewith are discussed below.

The preparation of C-4 functionalised precursors is known in the art and is, amongst other methods, achieved by the selective bromination at C-4 of compounds 1 and 2. Bromination is only possible with peracetates where the reactivity of the aromatic rings towards competing bromination is suppressed by electron withdrawing acetate groups. However, in order to control the degree of polymerization, protection at C-8 of the electrophilic species prior to condensation was required.

Other methods, which involve the introduction of sulphur or oxygen at C-4, have also been reported and have been used as an intermediate step for introducing a flavanyl or phenolic moiety at C-4 of flavan-3-ols for the production of proanthocyanidins and analogues thereof.

A further disadvantage associated with the prior art methods discussed herein above resides in the undesirable self-condensation of the C-4-functionalized precursors. This self-condensation of the precursors with a leaving group on C-4 has a significant effect on the degree of polymerization. Accordingly, the degree of polymerization is difficult to control such that a complex mixture of dimers, trimers, tetramers and higher oligomers as well as a complex mixture of analogues is formed. It will be appreciated that each C-4 functionalized precursor contains an electrophilic centre, with the result that after C—C bond formation between said precursor and a nucleophile, one electrophilic and one nucleophilic centre are present that are capable of reacting further and disadvantageously the degree of polymerization cannot be controlled. Where the precursor and a nucleophile are identical, a complex mixture of dimers, trimers, tetramers and higher oligomers is undesirably formed whilst a complex mixture of analogues is undesirably formed in the case of a non-identical precursor and nucleophile. The present invention allows for improved control over the degree of polymerisation and the lessening of self-polymerisation.

Yet a further disadvantage of previously known methods for the synthetic preparation of proanthocyanidins and analogues thereof involving the introduction of leaving groups on the C-4 carbon of flavan-3-ols, such as catechin or epicatechin, is that the known processes generally favours the predominant formation of 3,4-trans isomers of proanthocyanidins with generally very low yields of the 3,4-cis isomers. The present invention, in contrast, allows for greatly improved yields of the 3,4-cis isomers.

The term "flavonoid" is used in this description and dependent claims in its wider meaning which includes the compounds also known as flavanoids.

In this specification, the term "proanthocyanidin" denotes a compound which is essentially a multimer of from two to twenty identical monomeric units having flavonoid base structures and which are bonded together in a chain of such units by carbon to carbon interflavanyl bonds between a carbon of an aromatic ring of one unit and the C-4 carbon of another unit. Thus the compound catechin-(4β→8)-catechin is an example of a proanthocyanidin according to the meaning which that term denotes in this description of the invention and appended claims.

The expression "proanthocyanidin analogue" as used herein denotes a compound which is essentially composed of one to twenty monomeric units having flavonoid base structures and which, if there is more than one unit having a flavonoid base are bonded together in a chain of such units by carbon to carbon interflavanyl bonds between a carbon of an aromatic ring of one unit and the C-4 carbon of another unit, but wherein at least some of the flavonoid base monomeric units are dissimilar in structure from the others, and wherein one or more of the units may be a non-flavonoid base unit or units, provided that such non-flavonoid unit or units includes a nucleophilic aromatic moiety, and a carbon of such nucleophilic aromatic moiety forms an carbon to carbon bond with the C-4 carbon of a flavonoid base unit. Thus the compound (2R,4R)-4-(1,3,5-tri-O-methylphloroglucinol)-5,7,3'4'-tetra-O-methyl-flavan-3-one is an example of a proanthocyanidin analogue within the meaning ascribed to that expression for purposes of the present description and appended claims in respect of the present invention.

Also in this specification, the terms "dimer" and "trimer" respectively denote an association of two and three identical constituent units linked together, and the terms, oligomer and polymer have corresponding meanings. The formation of a dimer in accordance with the method of the present invention accordingly results in a proanthocyanidin.

Further, in this specification, the term "adduct" denotes an association of two non-identical constituent units linked together by means of carbon to carbon bonds. The formation of an adduct in accordance with the method of the present invention results in a proanthocyanidin analogue.

SUMMARY OF THE INVENTION

According to a first aspect of the invention, there is provided a method of introducing a nucleophilic aromatic moiety onto an unsubstituted C-4 carbon of a compound having a flavan-3-ol structure, comprising the steps of
  (a) converting the hydroxy group of the compound having the flavan-3-ol structure to an oxo group to form a flavan-3-one of that compound;
  (b) contacting the flavan-3-one of that compound with a compound containing the nucleophilic aromatic moiety in the presence of an oxidising agent;
  (c) allowing a carbon to carbon bond to form between the C-4 carbon of the flavan-3-one compound and a carbon of the nucleophilic aromatic moiety; and
  (d) reducing the flavan-3-one moiety to obtain the corresponding flavan-3-ol compound which is substituted by the nucleophilic moiety on the C-4 carbon.

According to a second aspect of the invention, there is provided a method of preparing a flavonoid having substituents on its C-3 and C-4 carbons in 3,4-cis configuration, comprising the steps of
  (a) providing a compound having a flavan-3-ol structure and which is unsubstituted on the C-4 carbon;
  (b) providing a compound having a nucleophilic aromatic moiety;
  (c) converting the hydroxy group of the compound having the flavan-3-ol structure to an oxo group to form a flavan-3-one of that compound;
  (d) contacting the flavan-3-one of that compound with a compound containing the nucleophilic aromatic moiety in the presence of an oxidising agent;
  (e) allowing a carbon to carbon bond to form between the C-4 carbon of the flavan-3-one compound and a carbon of the nucleophilic aromatic moiety;
  (f) reducing the flavan-3-one moeity to obtain the corresponding flavan-3-ol compound which is substituted by the nucleophilic aromatic moiety on the C-4 carbon in a mixture of the 3,4-cis and 3,4-trans configurations of that compound; and
  (g) separating the 3,4-cis and 3,4-trans configurations of the compound.

Where the flavan-3-ol compound used in the foregoing two methods contain reactive substituent groups that are prone to be reacted by the oxidation or reduction steps of those methods, such reactive substituent groups may be protected before the oxidation or reduction steps are performed, and such protective groups may be removed to restore the original substituent groups, if required.

The resultant product of the foregoing two methods may be further derivatised by replacing the C-3 hydroxy substituent or the C-4 nucleophilic aromatic moiety with any other substituent. Thus the resultant compound may be acetylated to convert the C-3 hydroxy group to an acetate group.

According to a specific application of the invention, there is provided a method for the preparation of proanthocyanidins and proanthocyanidin analogues, the method comprising the steps of
  (a) providing a 3-oxo-derivative of a flavan-3-ol, represented by Formula (I) (hereinafter referred to as "the 3-oxo-derivative"):

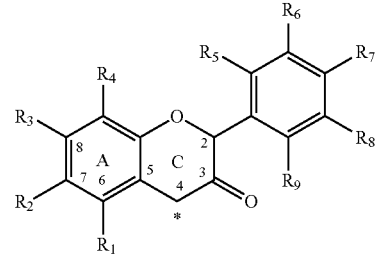

Formula (I)

wherein
  each of $R_1$, $R_2$, $R_3$, $R_4$, $R_5$, $R_6$, $R_7$, $R_8$ and $R_9$ is independently selected from the group consisting of —H, —OH, hydrocarbyl groups, saccharide moieties and —$OR_{10}$;
  wherein $R_{10}$ is selected from the group consisting of a hydrocarbyl group, an acyl group and a benzyl group; and
  wherein the hydrocarbyl groups in any one of $R_1$ to $R_{10}$ and the acyl group contains from 1 to 10 carbon atoms;
(b) providing an additional compound which is to constitute at least part of the proanthocyanidin or proanthocyanidin analogue, and which additional compound has a nucleophilic aromatic moiety (hereinafter referred to as "the additional compound");
(c) protecting each phenolic and each saccharide hydroxy group of the 3-oxo-derivative and of the additional compound to form a protected 3-oxo-derivative and protected additional compounds;
(d) contacting the protected 3-oxo-derivative or the 3-oxo-derivative without any phenolic hydroxy groups or saccharide hydroxy groups with the protected additional compound or additional compound without any phenolic or saccharide hydroxy group in the presence of an oxidising agent;

(e) allowing a direct C—C bond to form between with the carbon atom in the 4-position of the 3-oxo-derivative (shown by "*" in Formula (I)) and a carbon atom which is part of the nucleophilic aromatic moiety of the additional compound;

(f) optionally, and where the additional compound has a flavonoid base structure having no substituent at its C-4 position and a hydroxy group at its C-3 position, oxidising the hydroxide group to provide a secondary 3-oxo-derivative;

(g) and further optionally providing a secondary additional compound which is to constitute at least part of the proanthocyanidin or proanthocyanidin analogue, and which secondary additional compound has a nucleophilic aromatic moiety (hereinafter referred to as "the secondary additional compound");

(h) contacting the secondary 3-oxo-derivative with the secondary additional compound in the presence of an oxidising agent;

(i) optionally repeating the steps (f), (g) and (h) as many times as is necessary to achieve the incorporation of the desired number of monomeric units in the resultant proanthocyanidin or proanthocyanidin analogue;

(j) further optionally reducing the resulting proanthocyanidin or proanthocyanidin analogue to convert the oxo group on the various C-3 positions of the respective 3-oxo derivative units introduced into the resultant products to a hydroxide group; and (k) optionally removing any or all of the phenolic or saccharide hydroxy protecting groups to yield the unprotected hydroxy compounds.

It will be appreciated by the skilled person that the stereochemistry at C-2 of the compound of Formula (I) allows for the product of Formula (I) to exist in alpha or beta form or as a mixture of both. It will be further appreciated that the aforesaid stereochemistry of the compound of Formula (I) affords an enantiomerically pure and optically active product.

The 3-oxo-derivative of flavan-3-ol may be prepared from a flavan-3-ol wherein the hydroxy group at the 3 position of flavan-3-ol is oxidised to an oxo group. This may be achieved by any means known in the art. Such preparation may, for example, be effected by the procedure known as Dess-Martin oxidation. It is envisaged that by doing so, the 3-oxo-derivative has enhanced electrophilicity at C-4 by virtue of the C-3 oxo substituent.

The hydrocarbyl groups from which $R_1$-$R_{10}$ may be selected may be linear hydrocarbyl groups or cyclic hydrocarbyl groups.

The linear hydrocarbyl groups may be selected from the group consisting of methyl, ethyl, propyl, butyl, pentyl, hexyl, heptyl, octyl, nonyl, and decyl.

The cyclic hydrocarbyl may be selected from the group consisting of cyclopropyl, cyclobutyl, cyclopentyl, cyclohexyl, cycloheptyl, cyclooctyl, cyclononyl, and cyclodecyl.

The hydrocarbyl groups from which $R_{10}$ may be selected are preferably a benzyl group or an acyl group The saccharide moieties may be selected from the group consisting of monosaccharides, disaccharides, oligosaccharides, polysaccharides and analogues of these saccharides.

The compound having a nucleophilic aromatic moiety may be a compound having a phenolic, flavanyl or flavonoid moiety.

Where the compound having a nucleophilic aromatic moiety is a compound having a phenolic moiety, the compound containing said phenolic moiety (hereinafter referred to as the "phenolic species") is preferably 1,3,5 tri-methoxybenzene. The coupling of the 3-oxo-derivative and the phenolic species results in the formation of a 4-aryl-flavan-3-one adduct comprising the 3-oxo-derivative and the phenolic moieties.

Where the compound having a nucleophilic aromatic moiety is a compound having a flavanyl or flavonoid moiety, the compound containing said flavanyl or flavonoid moiety (hereinafter referred to as the "flavanol species") is preferably flavan-3-ol, most preferably 5,7,3',4'-tetra-O-methylcatechin. The coupling of the 3-oxo-derivative and the flavanol species results in the formation of an adduct comprising the 3-oxo-derivative and the flavanol or flavonoid moieties.

It will be appreciated by the person skilled in the art that compounds having other suitable nucleophilic aromatic moieties may be used without departing from the spirit and scope of the invention.

The oxidising agent may be selected from the group consisting of $AgBF_4$, $Pb(OAc)_4$, DDQ, $OsO_4$, Tollens reagent, $KMnO_4$, and pyridinium chlorochromate In a preferred embodiment of the invention, the oxidising agent is $AgBF_4$. $AgBF_4$ is a weak oxidising agent with a $(BF_4)^-$ counterion. The highest yields were obtained with $AgBF_4$ and, without wishing to be bound by theory, it is suggested that the $(BF_4)^-$ counterion facilitates stabilization of quinine methide intermediates formed during the C—C bond formation.

The compound having a nucleophilic aromatic moiety, the 3-oxo-derivative and the oxidising agent may be mixed together in the presence of a solvent. The solvent is preferably selected from the group consisting of tetrahydrofuran (herein referred to as "THF"), diethyl ether or any aprotic solvent that is capable of dissolving said compound and the 3-oxo-derivative that are to be coupled via a C—C bond.

In a preferred embodiment of the invention, $R_1$, $R_3$, $R_6$ and $R_7$ are the same and $R_2$, $R_4$, $R_5$, $R_8$ and $R_9$ are H. Preferably each of $R_1$, $R_3$, $R_6$ and $R_7$ are $OR_{10}$, wherein $R_{10}$ is —$CH_3$ and C-2 is in the (2R) configuration. In such a case, the 3-oxo-derivative is tetra-O-methyl-3-oxo-catechin represented by Formula (II):

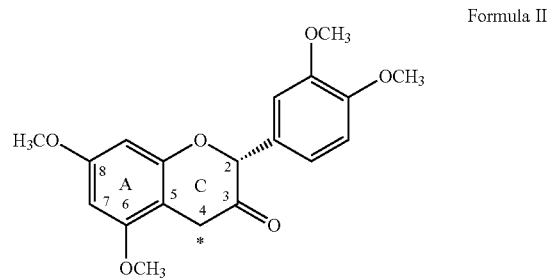

Formula II

By oxidising flavan-3-ol to the 3-oxo-derivative, the reactivity of the benzene ring "A" in Formulae (I) and (II) is decreased to such a degree that self-condensation between atoms of the 3-oxo-derivative and the compound having the nucleophilic aromatic moiety is avoided. This, in turn, allows for the isolation of the adduct that forms when the 3-oxo derivative couples to the nucleophilic aromatic moiety of the compound.

Where a phenolic species which is not the same as the 3-oxo-derivative is contacted with the 3-oxo-derivative, the resulting adduct is an analogue of proanthocyanidin represented by Formula (III):

Formula (III)

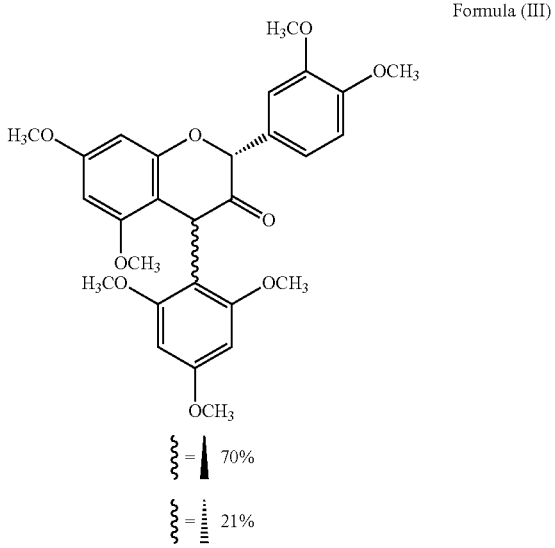

Where a flavanol species is contacted with the 3-oxo-derivative, the resulting proanthocyanidin is represented by Formula (IV):

Formula (IV)

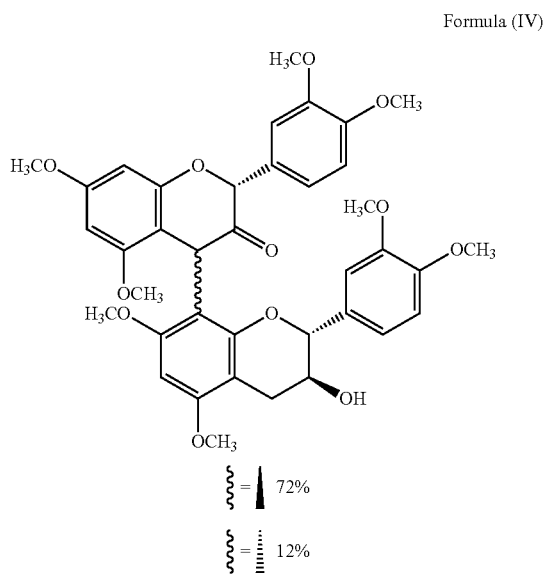

The resulting compounds represented by Formulae (III) and (IV) may be subjected to reduction, particularly metal hydride reduction wherein cis- and trans-diastereomers of the adducts are formed. Surprisingly, metal hydride reduction affords predominantly 3,4-cis stereochemistry of the compounds. During this reduction step, the oxo group at the 3 position of the 3-oxo-derivate is replaced by a hydroxy group. The metal hydride reduction may take place according to any means known in the art. In a preferred embodiment of the invention, $NaBH_4$ is used to achieve metal hydride reduction of the adduct. As alluded to above, reduction of the carbonyl group takes place stereoselectively in such a way that the 3,4-cis isomer is predominantly formed. A mixture of flavonoid compounds prepared by the method of the invention described herein above having substituents on its C-3 and C-4 carbons in which the 3,4-cis configuration of such compounds are present in a greater quantity than the 3,4-trans configuration of such compounds is accordingly a further aspect of this invention.

The invention further provides for the resulting compound with a flavanol moiety (Formula (IV)) to be subjected to oxidation wherein the hydroxy group at the 3 position of the flavanol species (which species is coupled to the 3-oxo derivative) is oxidized to an oxo group in order to activate the C-4 of the coupled flavanol species. This activated dimer may then be contacted with a further compound having a nucleophilic aromatic moiety of the type described herein above in the presence of a oxidising agent, preferably $AgBF_4$, as herein before described to yield a trimer. In this way, controlled polymerisation is achieved. In the absence of said oxidation, the resultant adduct is unable to undergo further reaction.

According to a further embodiment of the invention and where $R_{10}$ is benzyl, hydrogenation may be employed after coupling so as to remove the phenyl groups. Where $R_{10}$ is acetate, said acetate may be removed by means of a weak acid or base. In this way, free phenolic proanthocyanidins and analogues thereof may be produced.

These and other features of the invention are described in more detail below.

EXAMPLES OF THE INVENTION

The invention will now be described with reference to the following non-limiting examples.

General Information:
NMR Spectra

NMR experiments were carried out on a Brucker Avance spectrometer (600 MHz). $SiMe_4$ was added as reference to all NMR samples.

Mass Spectra

High-resolution mass spectra were recorded at 70 eV on a VG 70 SEQ mass spectrometer with a MASPEC II data system.

Spraying Reagent:

2% v/v solution of formaldehyde (40%) in concentrated $H_2SO_4$.

Abbreviations of TLC Solvents:

A=acetone, DCM=dichloromethane, EtOAc=ethyl acetate, EtOH=ethanol, H=hexane, MeOH=methanol, T=tolueen.

IR Spectra:

IR spectra were recorded on a Bruker Tensor 27 FT-IR single beam instrument. The standard sample cell used was a Pike Miracle single-bounce attenuated total reflectance (ATR) cell equipped with a ZnSe single crystal. Measurements were taken over a range of 400 $cm^{-1}$ to 4000 $cm^{-1}$, no carrier was used and a background run was performed in each case.

Example 1

A 3-oxo-derivative of flavan-3-ol (compound 4) was prepared from flavan-3-ol as shown in Scheme 1 below.

Scheme 1

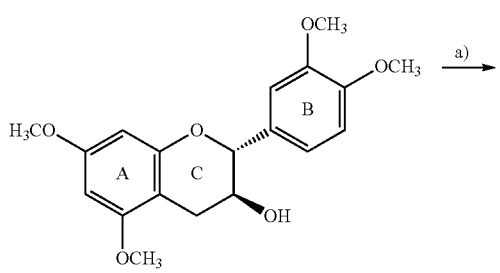

3

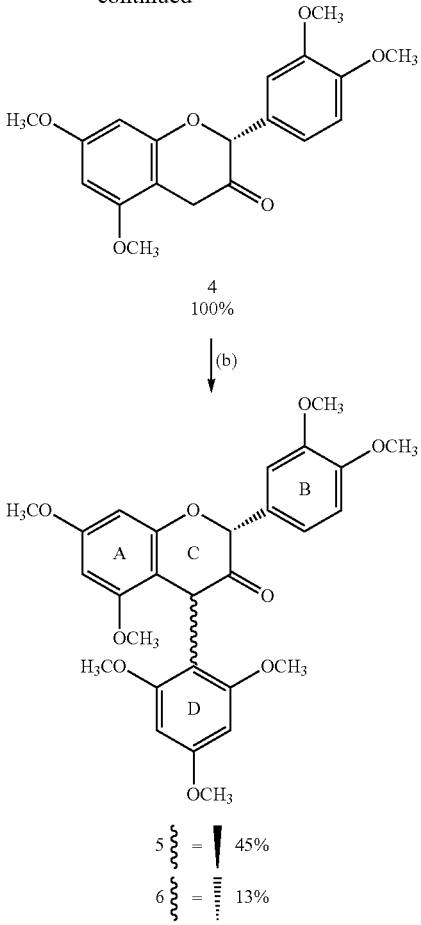

a) Dess martin Periodinane, moist CH₂Cl₂, RT, 45 min
b) 1,3,5-tri-O-methylphloroglucinol Referring to Scheme 1, flavan-3-ol, more particularly 5,7,3',4'-Tetra-O-methylcatechin (compound 3), was prepared as follows:

Dried (+)-catechin (10 g, 35 mmol) was dissolved in dry acetone (250 mL) under an inert atmosphere ($N_2$). $K_2CO_3$ (38 g, 276 mmol) was added and suspended in the reaction mixture. After stirring for 1 hour, dimethylsulfate (87 mg, 276 mmol) was slowly added over a period of 30 min. and the reaction mixture refluxed for 2 hours. The $K_2CO_3$ was filtered off, the acetone removed under reduced pressure and the excess $(CH_3)_2SO_4$ destroyed with cold ammonia (80 mL, 25% $NH_3/H_2O$, v/v). The reaction mixture was subsequently extracted with ethyl acetate (2×100 mL), washed with water (2×70 mL) and brine (70 mL), dried over $MgSO_4$ and the solvent removed under reduced pressure. The compound 3 was obtained as an off-white, amorphous solid (11.9 g, 99%).

Compound 3 was then subjected to an oxidation step to prepare the 3-oxo-derivative, more specifically (2R)-5,7,3'4'-tetrakis(methyloxy)flavan-3-one (compound 4). This was achieved as follows:

Under a $N_2$ atmosphere, Dess-Martin periodinane (7.5 mL, 0.3 M solution of DMP in DCM) was added to a solution of compound 3 (560 mg, 1.6 mmol) in dry $CH_2Cl_2$ (5 mL). After stirring for 5 min., moistened $CH_2Cl_2$ (20 mL) was added dropwise over 45 min resulting in a cloudy reaction mixture. The reaction mixture was extracted with ether (30 mL), washed with a mixture of 10% $Na_2S_2O_3$ and saturated $NaHCO_3$ (2×30 mL, 1:1, v/v) and the two layers separated. The water phase was extracted with ether (20 mL), the combined organic phases washed with water and brine, dried over anhydrous sodium thiophosphate and the solvent removed under vacuum. The crude product was filtered over $SiO_2$ (4×4 cm, H:EtOAc 6:4) and crystallized from the eluant as white needles. Yield: 451 mg, 95% (85 mg compound 4 recovered).

With reference to Scheme 1 and in the embodiment of the invention where the nucleophilic aromatic moiety is a phenolic moiety, the phenolic species in the form of 1,3,5 trimethoxybenzene, the 3-oxo-derivative, more specifically (2R)-5,7,3'4'-tetrakis(methyloxy)flavan-3-one (compound 4), is contacted therewith in the presence of $Ag(BF_4)^-$ in THF to form C-4 phloroglucinol adducts (compound 5) (45%) and compound 6 (13%), particularly (2R,4S)- and (2R,4R)-4-(1,3,5-tri-O-methylphloroglucinol)-5,7,3'4'-tetra-O-methyl-flavan-3-ones, respectively as shown in Scheme 1. The C-4 phloroglucinol adducts were obtained as follows:

Under a $N_2$ atmosphere, compound 4 (50 mg, 0.145 mmol) and $Ag(BF_4)^-$ (215 mg, 1.1 mmol) were dissolved in THF (2 mL). A solution of 1,3,5-tri-O-methylphloroglucinol (50 mg, 0.093 mmol) in THF (3 mL) was added dropwise and the reaction mixture refluxed for one hour. After concentrating the reaction mixture under vacuum, it was filtered on $SiO_2$ (2 cm×4 cm, H:EtOAc 6:4) and subsequently separated on $SiO_2$ (T:EtOAc 8:2) to afford compound 5 ($R_f$ 0.40, 34 mg, 70%) and compound 6 ($R_f$ 0.30, 9 mg, 21%).

The characteristics of the spectra for the C-4 phloroglucinol adducts are set out hereunder.

Compound 5:
Found M⁺ 510.18842, $C_{28}H_{30}O_9$ requires M⁺ 510.18898, (M+H)⁺ 5$\overline{11}$ (43), m/z 343 (100), 315 (22), 2$\overline{87}$ (10). IR: $v_{max}$ $\overline{2959}$, 1724, 1593 cm⁻¹. ¹H NMR: δ (CDCl₃) 3.51-3.84 (s, 21H, 7×OCH₃), 5.10 (s, 1H, 4-H), 5.63 (d, J=0.5 Hz, 1H, 2-H), 5.99 (d, J=2.0 Hz, 2H, 6-H), 6.10 (s, 2H, 3"/5"-H), 6.31 (d, J=2.0 Hz, 1H, 8-H), 6.77 (d, J=8.0 Hz, 1H, 5'-H), 6.90 (dd, J=2.0, 8.0 Hz, 1H, 6'-H), 6.94 (d, J=2.0 Hz, 1H, 2'-H). ¹³C NMR: δ (CDCl₃) δ8.1 (C-4), 55.2-55.9 (7×OCH₃), 82.8 (C-2), 91.0 (C-3"/5"), 92.8 (C-6), 94.1 (C-8), 106.1, 109.4 (C-2'), 111.1 (C-5'), 111.3 (C-6'), 118.3 (C-1"), 128.1 (C-1'), 148.8 (C-3'), 149.0 (C-4'), 154.1, 158.4 (C-2"/6"), 158.7, 160.0 (C-4"), 160.1 (C-7), 206.4 (C-3). CD: λ nm (θ), 184.60 (6.573×10³), 194.20 (7.232×10³), 200.40 (−8×10³), 211.60 (6.762×10⁴), 237.20 (3.221×10⁴), 258.60 (5.108×10³), 290.00 (8.759×10³).

Compound 6:
Found M⁺ 510.18826, $C_{28}H_{30}O_9$ requires M⁺ 510.18898, (M+H)⁺ 5$\overline{11}$ (68), m/z 343 (100), 315 (82), 2$\overline{87}$ (53). IR: $v_{max}$ $\overline{2925}$, 1731, 1594 cm⁻¹. ¹H NMR: δ (CDCl₃) 3.58-3.89 (s, 21H, 7×OCH₃), 5.24 (d, J=2 Hz, 1H, 4-H), 5.34 (d, J=2 Hz, 1H, 2-H), 6.07 (d, J=2.0 Hz, 1H, 6-H), 6.08 (s, 2H, 3"/5"-H), 6.27 (d, J=2.0 Hz, 1H, 8-H), 6.89 (d, J=8.0 Hz, 1H, 5'-H), 6.96 (d, J=2.0 Hz, 1H, 2'-H), 6.98 (dd, J=2.0, 8.0 Hz, 1H, 6'-H). ¹³C NMR: δ (CDCl₃) 29.4, 40.4 (C-4), 54.9-55.9 (7×OCH₃), 84.8 (C-2), 91.2 (C-3"/5"), 93.4 (C-6), 93.8 (C-8), 107.8, 110.9 (C-5'), 111.2 (C-1"), 111.7 (C-2'), 121.5 (C-6'), 127.8 (C-1'), 148.9 (C-4'), 149.4 (C-3'), 156.5, 158.5 (C-2"/6"), 158.8 (C-4"), 159.7 (C-5), 160.1 (C-7), 205.2 (C-3). CD: nm (θ), 210.50 (−5.362×10⁴), 233.00 (−1.464×10⁴), 273.50 (5.963× 10³), 293.00 (6.651×10³), 344.50 (4.432×10³).

The requirement of an excess of AgBF₄ and the observation of a silver mirror (reduction of Ag¹ to Ag⁰) indicates a two electron oxidative mechanism as shown in Scheme 2 set out below.

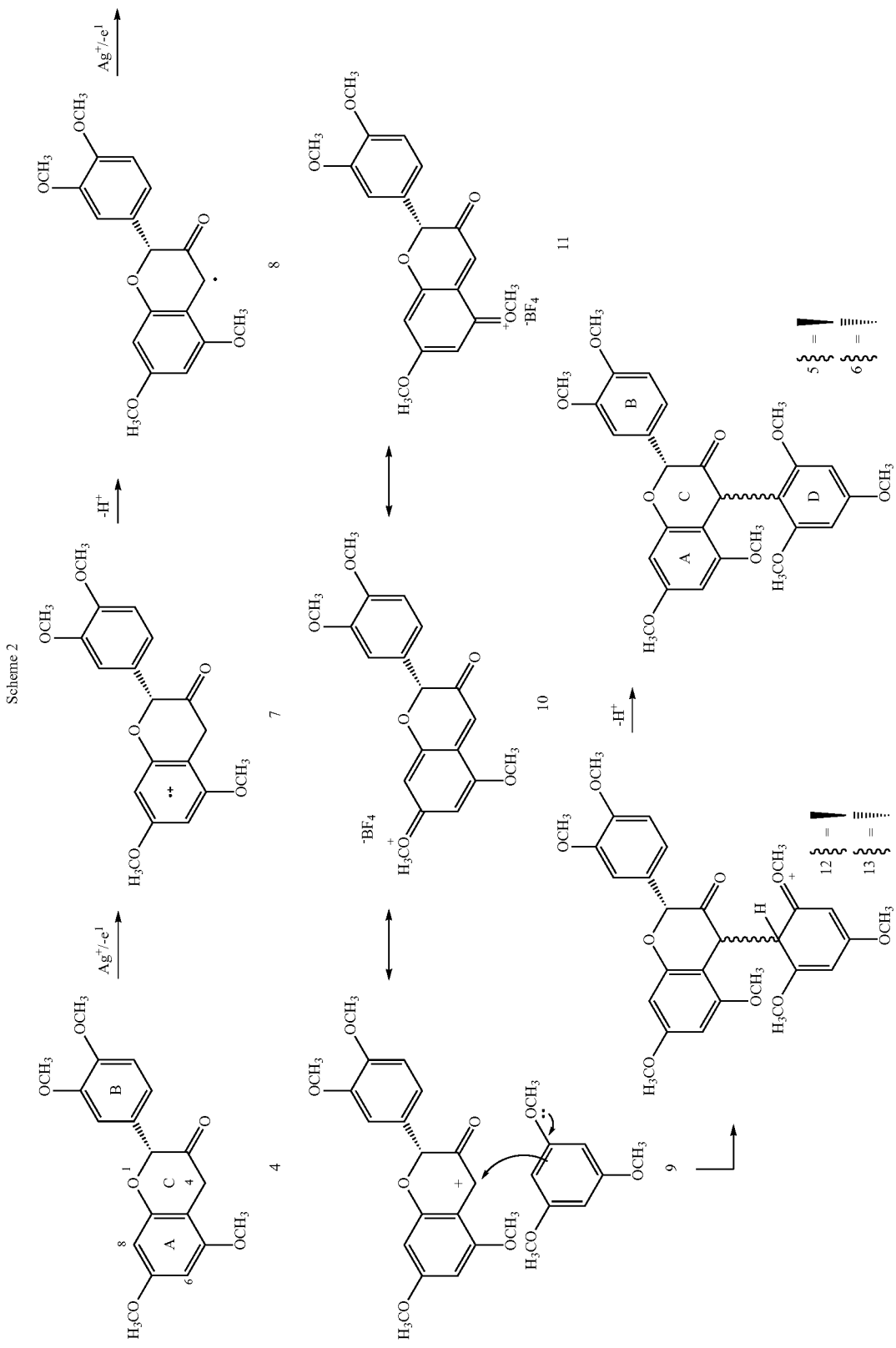

With reference to Scheme 2, the intermediary carbocation (compound 9) is both benzylic and alpha to a carbonyl group. Further stabilization of compound 9 or its quinone methide tautomers (compounds 10 and 11) by the non-nucleophilic $(BF_4)^-$ counter-ion is feasible.

Subsequent reduction of compounds 5 and 6 with $NaBH_4$ in aqueous NaOH/MeOH afforded the 4-arylflavan-3-ol derivatives, compound 14 (98%) and compound 16 (95%), respectively.

This is shown in Scheme 3.

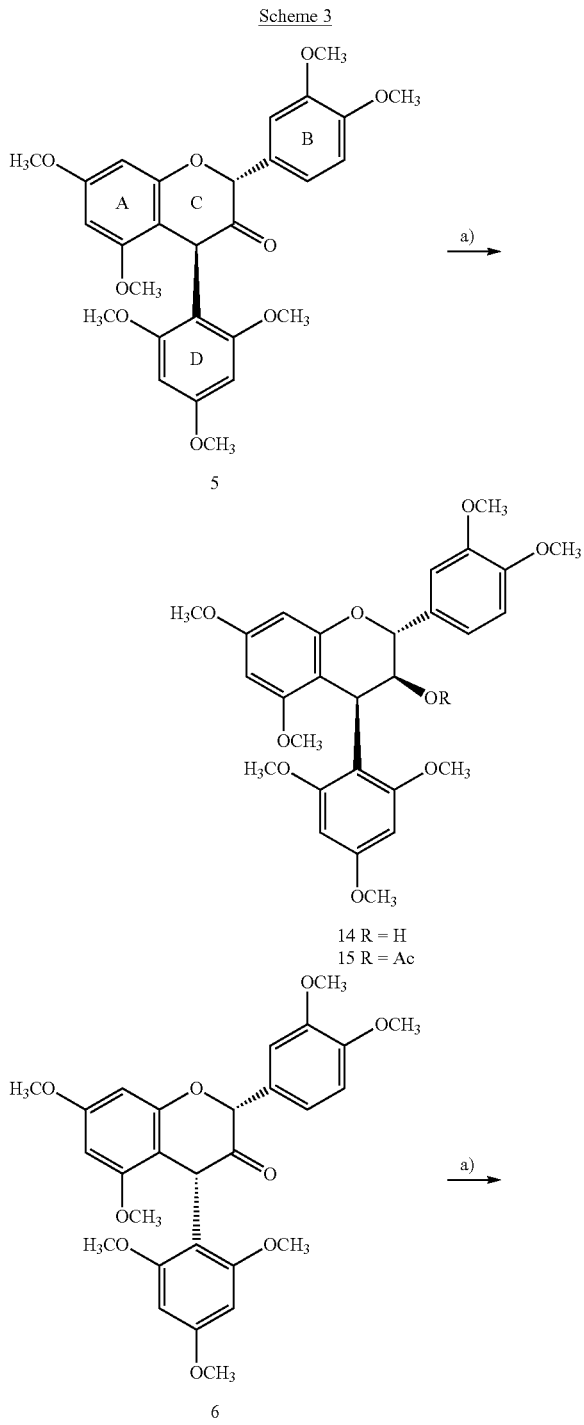

Scheme 3

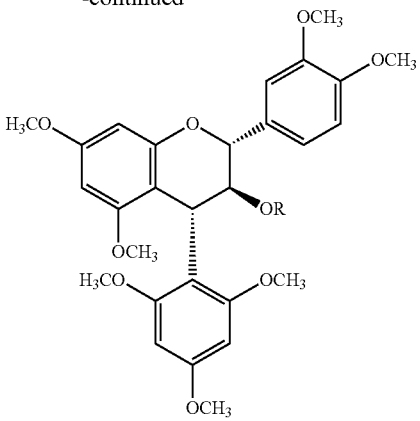

16 R = H
17 R = Ac a) $NaBH_4$, MeOH, aqNaOH, 0° C., 10 min.

More specifically, (2R,3S,4S)- and (2R,3S,4R)-4-(1,3,5-tri-O-methylphloroglucinol)-5,7,3'4'-tetra-O-methylflavan-3-ol (compounds 14 and 16), were prepared as follows:

An aqNaOH solution (10 ml, 2.00 M) was added to ethanol (200 mL) followed by $NaBH_4$ (7.71 g, 0.20 mol). To a solution of compound 5 (20 mg, 0.04 mmol) in ethanol (5 mL) was slowly added the $NaBH_4$ solution (1 mL) prepared above. After stirring the reaction mixture for 5 min. the ethanol was removed under reduced pressure, the excess $NaBH_4$ destroyed with water (1 mL) and the subsequent mixture extracted with ether (2×10 mL). The organic phase was washed with water (10 mL), dried over $MgSO_4$ and evaporated to dryness under vacuum to yield compound 14 (20 mg, 98%) as a white, amorphous solid.

Compound 16 was prepared in exactly the same way.

$^1H$ NMR coupling constants and CD data permitted assignment of (2R,3S,4S) and (2R,3S,4R) absolute configuration for compounds 14 and 16, respectively.

The characteristics of the spectra for the C-4 phloroglucinol adducts are set out hereunder.

Compound 14:

Found $M^+$ 512.20408, $C_{28}H_{32}O_9$ requires $M^+$ 512.20463, ( $M+H)^+$ 513 (58), m/z 345 (76), 333 (100), 317 (72), 303 (20), 191 (22). IR: $v_{max}$ (3515, 2936, 2836, 1607 cm$^{-1}$. $^1H$ NMR: δ (CDCl$_3$) 3.35-3.87 (7×s, 21H, 7×OCH$_3$), 4.23 (dd, J=6.3, 9.0 Hz, 1H, 3-H), 4.94 (d, J=6.3 Hz, 1H, 4-H), 4.96 (d, J=9.0 Hz, 1H, 2-H), 6.01 (d, J=2.4 Hz, 1H, 6-H), 6.14 (very br. s, 1H, H-3"/5"(D)) 6.21 (very br. s, 1H, H-3/5(D)), 6.19 (d, J=2.4 Hz, 1H, 8-H), 6.23 (very br. s, 1H, 3"15"-H), 6.85 (d, J=9.0 Hz, 1H, 5'-H), 6.98 (d, J=2.0 Hz, 1H, 2'-H), 6.99 (dd, J=2.0, 9.0 Hz, 1H, 6'-H). $^{13}C$ NMR: δ (CDCl$_3$) 32.2 (C-4), 55.2-56.3 (6×s, 7×OCH$_3$), 71.8 (C-3), 78.2 (C-2), 91.4 (C-8), 91.9 (C-3"/5"), 92.7 (C-6), 93.6 (C-3"/5"), 105.5, 109.8, 110.4 (C-2'), 111.0 (C-5'), 120.2 (C-6'), 132.0, 148.9, 149.0, 156.3, 158.2, 159.5, 160.0. CD: □ nm (θ), 211.60 (6.762×10$^4$), 237.20 (3.221×10$^4$), 258.60 (5.108×10$^3$), 290.00 (8.759×10$^3$).

Compound 16:

Found $M^+$ 512.20406, $C_{28}H_{32}O_9$ requires $M^+$ 512.20463, ( $M+H)^+$ 513 (60), m/z 345 (80), 333 (100), 317 (75), 191 (21). IR: $v_{max}$ 3526, 2941, 2828, 1598 cm$^{-1}$. $^1H$ NMR: δ (DMSO) 3.28-3.78 (7×s, 21H, 7×OCH$_3$), 3.98 (m, 1H, 3-H), 4.21 (d, J=6.0 Hz, 1H, 4-H$_{rot.}$), 4.81 (d, J=6.5 Hz, 1H, 4-H), 4.85 (d, J=10.0 Hz, 1H, 2-H), 5.99 (d, J=2.3 Hz, 1H, H-6), 6.02 (d, J=10.0 Hz, 1H, 8-H), 6.14 (br s, 1H, 3"/5"-H), 6.25 (br s, 1H, 3"/5"-H), 6.86 (dd, J=1.8, 8.3 Hz, 1H, 6'-H), 6.90 (d, J=1.8 Hz, 1H, 2'-H), 6.91 (d, J=8.3 Hz, 1H, 5'-H). $^{13}$C NMR: δ (DMSO): 32.1 (C-4), 55.4-56.9 (6×s, 7×OCH$_3$), 70.40 (C-3), 78.4 (C-2), 91.15 (C-6), 92.7 (C-3"/5"), 93.0 (C-8), 93.8 (C-3"/5"), 106.1, 111.4, 111.7, 112.0 (C-5'), 120.8 (C-6'), 133.4, 148.7, 148.8, 156.5, 158.2, 159.4, 159.5, 160.0, 160.6. CD: □ nm (θ), 210.50 (-5.362×10$^4$), 233.00 (-1.464×10$^4$), 273.50 (5.963×10$^3$), 293.00 (6.651×10$^3$), 344.50 (4.432×10$^3$).

Example 2

In the embodiment of the invention wherein the nucleophilic aromatic moiety of the compound is a flavanyl moeity, the flavanol species, in the form of favan-3-ol, was contacted with the 3-oxo-derivative to form a proanthocyanidin adduct. More particularly, compound 3 and compound 4 of scheme 1, prepared in the manner herein described, were contacted with each other in the presence of AgBF$_4$ in THF as a solvent to produce (2R,4S:2R,3S)-5,7,3'4'-tetra-O-methylflavan-3-one-[4→8]-5,7,3',4'-tetra-O-methyl-flavan-3-ol (compound 18) and (2R,4R:2R,3S)-5,7,3'4'-tetra-O-methylflavan-3-one-(4→8'-5,7,3',4'-tetra-O-methylflavan-3-ol (compound 19), respectively. This is shown in Scheme 4 below.

SCHEME 4

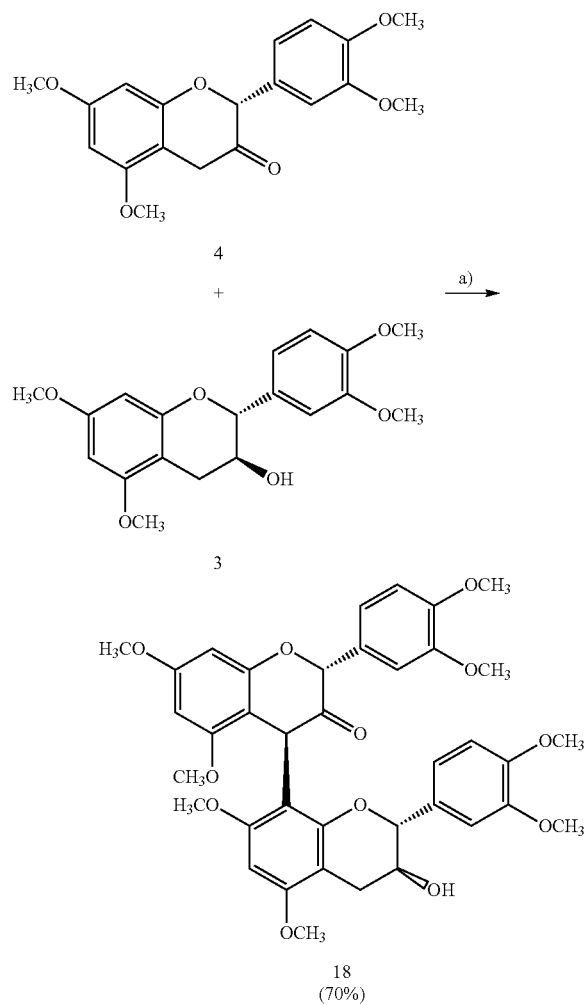

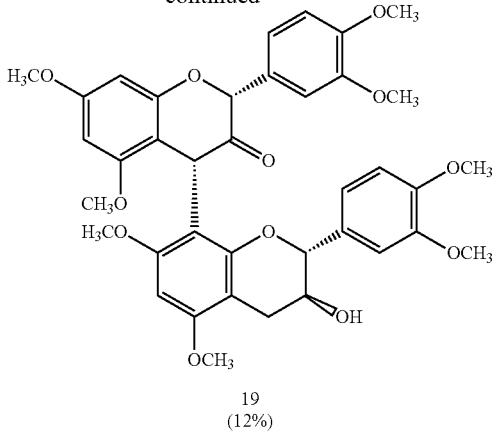

a) AgBF$_4$, THF, RT

With reference to Scheme 1 and Scheme 4 compounds 18 and 19 were prepared as follows:

Under a N$_2$ atmosphere compound 4 (50 mg, 0.145 mmol) and AgBF$_4$ (215 mg, 1.1 mmol) were dissolved in THF (3 mL). A solution of compound 3 (150 mg, 0.435 mmol) in THF (3 mL) was added dropwise and the reaction mixture refluxed for 4 hours. The reaction mixture was filtered on SiO$_2$ (2×4 cm, T:A 7:3) and subsequently separated by PLC (T:A 7:3) to afford compound 18 (R$_f$ 0.32, 68 mg, 72%) and compound 19 (R$_f$ 0.12, 12 mg, 12%), respectively.

The characteristics of the spectra for the C-4 phloroglucinol adducts are set out hereunder.

Compound 18

Found M$^+$ 688.23363, C$_{38}$H$_{40}$O$_{12}$ requires M$^+$ 688.25198, [M+H]$^+$ 689 (96) m/e 509 (52), 343 (100), 315 (28), 287 (19). IR: ν$_{max}$ 2939, 2838, 1720, 1611 cm$^{-1}$. $^1$H NMR: (CDCl$_3$) 2.55 [dd, J=9.4, 16.2 Hz, 1H, 4-H(F)], 3.06 [dd, J=5.6, 16.2 Hz, 1H, 4-H(F)], 3.53-3.89 (8×s, 24H, 8×OCH$_3$), 3.93 [m, 1H, 3-H (F)], 4.49 [d, J=8.5, 1H, 2-H (F)], 5.09 [s, 1H, 4-H(C)], 5.39 [s, 1H, 2-H(C)], 5.98 [d, J=2.4 Hz, 1H, 6-H (A)], 6.09 [d, J=2.4 Hz, 1H, H-8(A)], 6.11 [s, 1H, 6-H (D)], 6.70 [d, J=8.4 Hz, 1H, 5-H(B)], 6.79 [ddd, J=1.0, 2.0, 8.4 Hz, 1H, 6-H(B)], 6.83 [d, J=2.0 Hz, 1H, 2-H(B)], 6.88 [d, J=8.8 Hz, 1H, 5-H(E)], 6.94 [dd, J=2.0, 8.8 Hz, 1H, 6-H(E)], 6.94 [d, J=2.0 Hz, 1H, 2-H(E)]. $^{13}$C NMR: δ (CDCl$_3$) 27.8 (C-4 (F)), 30.9, 38.2 (C-3(F)), 55.3-56.2 (8×OCH$_3$), 68.8 (C-4 (C)), 81.6 (C-2(F)), 82.6 (C-2(C)), 88.6 (C-6(D)), 92.8 (C-8 (A)), 94.0 (C-6(A)), 101.8, 106.1, 109.3 (C-2(B)), 110.0, 110.1 (C-2(E)), 110.9 (C-5(E)), 111.1 (C-5(B)), 118.2 (C-6 (B)), 119.6 (C-6(E)), 128.0 (C-1(B)), 130.7 (C-1(E)), 148.7 (C-3(B)), 148.9 (C-4(B)), 149.0 (C-3(E)), 149.1 (C-4(E)), 152.4 (C-8(D)), 154.2 (C-5(D)), 156.9, 157.1 (C-7(D)), 158.6 (C-5(A)), 159.8 (C-7(A)), 206.1 (C-3). CD: □ nm (θ), 202.00 (4.076×10$^4$), 214.20 (1.445×10$^5$), 237.60 (6.305×10$^4$), 259.00 (1.141×10$^4$), 289.20 (1.659×10$^4$), 348.20 (-1.932×10$^3$).

Compound 19:

Found M$^+$ 688.24550, C$_{38}$H$_{40}$O$_{12}$ requires M$^+$ 688.25198, [M+H]$^+$ 689 (100) m/e 509 (30), 343 (86), 315 (20), 287 (14). IR: ν$_{max}$ 2935, 2838, 1720, 1612, 1517 cm$^{-1}$. $^1$H NMR: δ (CDCl$_3$) 2.62 (dd, J=7.3, 16.5 Hz, 1H, 4-H(F)$_{ax}$), 2.83 (dd, J=5.2, 16.5 Hz, 1H, 4-H(F)$_{eq}$), 3.63-3.88 (8×s, 24H, 8×OCH$_3$), 4.04-4.08 [m, 1H, 3-H(F)], 4.85 [d, J=6.5 Hz, 1H, 2-H(F)], 5.19 [d, J=1.4 Hz, 1H, 2-H(C)], 5.42 [s, 1H, 4-H(C)], 6.08 [d, J=2.4 Hz, 1H, 6-H(A)], 6.09 [s, 1H, 6-H(D)], 6.14 [d, J=2.4 Hz, 1H, 8-H(A)], 6.72 [dd, J=1.9, 8.3 Hz, 1H, 6-H(E)], 6.77 [d, J=8.3 Hz, 1H, 5-H(E)], 6.80 [d, J=1.90 Hz, 1H, 2-H(E)], 6.84 [dd, J=1.6, 8.1 Hz, 1H, 6-H(B)], 6.85 [d, J=8.1 Hz, 1H, 5-H(B)], 6.88 [d, J=1.6 Hz, 1H, 2-H(B)]. $^{13}$C NMR: δ (CDCl$_3$) 26.4 (C-4(F)), 30.9 (C-3(F)), 40.6 (C-4(C)), 55.3–56.2 (8×OCH$_3$), 68.1, 81.4 (C-2(F)), 84.7 (C-2(C)), 89.0 (C-6 (D)), 93.5 (C-6(A)), 94.0 (C-8(A)), 101.2, 107.8, 109.4 (C-2 (E)), 109.9, 111.0 (C-5(B)), 111.1 (C-5(E)), 112.0 (C-2(B)), 119.1 (C-6(E)), 121.4 (C-6(B)), 127.6, 130.9, 148.9, 149.0, 149.1, 149.4, 152.4, 156.6, 156.7, 157.3, 158.9, 159.7, 206.1 (C-3). CD: □ nm (θ), 183.20 (3.958×10$^3$), 188.80 (−1.789× 10$^3$), 192.60 (7.21×10$^2$), 195.00 (−6.758×10$^2$), 202.20 (4.926×10$^4$), 211.80 (−4.122×10$^3$), 289.80 (1.573×10$^4$).

Metal hydride reduction of compound 18 afforded the 2,3-trans-3,4-cis octa-O-methyl ether of catechin-[4β→8]-catechin 20. This is shown in Scheme 5 below.

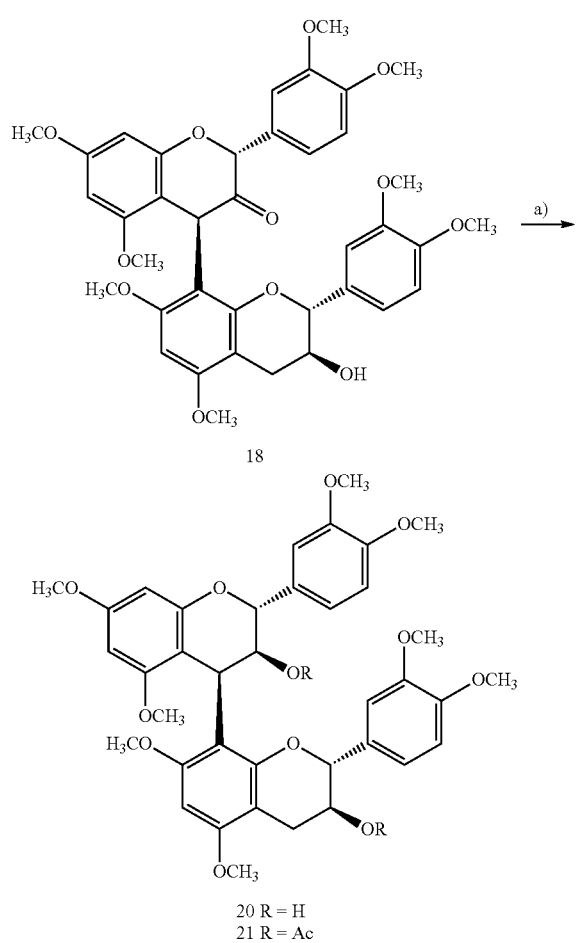

Scheme 5

20 R = H
21 R = Ac a) NaBH$_4$, MeOH, aqNaOH, 0° C., 10 min.

More specifically, compounds 20 and 21 were prepared as follows:

(2R,3S,4S:2R,3S)-5,7,3'4'-tetra-O-methylflavan-3-ol-[4→8]-5,7,3',4'-tetra-O-methyl-flavan-3-ol (compound 20): An aqNaOH solution (10 ml, 2.00 M) was added to 200 ml ethanol followed by NaBH$_4$ (7.71 g, 0.20 mol). To a solution of compound 18 (18 mg, 0.03 mmol) in methanol (5 mL) was slowly added the above mentioned NaBH$_4$ solution (1 mL). After stirring the reaction mixture for 5 min. the methanol was removed under reduced pressure, the excess NaBH$_4$ destroyed with water (1 mL) and the subsequent mixture extracted with ethylacetate (2×10 mL). The organic phase was washed with water (10 mL), dried over MgSO$_4$ and evaporated to dryness under vacuum. PLC (toluene:ethylacetate; 5:5) yielded compound 20 (21 mg, 97%, R$_f$ 0.42) as a white, amorphous solid. Acetylation of compound 20 afforded the octamethyl ether diacetate (compound 21) as a white amorphous solid (23 mg, 100%)

The characteristics of the spectra for the C-4 phloroglucinol adducts are set out hereunder.

Compound 20:
Found M$^+$ 690.26917, C$_{38}$H$_{42}$O$_{12}$ requires M$^+$ 690.26763, [M+H]$^+$ 691 (100) m/e 511 (32), 495 (12), 345̄ (35). IR: v$_{max}$ 2927, 2837, 1700, 1595, 1518 cm$^{-1}$. $^1$H NMR: δ (DMSO, 145° C.) 2.53 (dd, J=6.9, 16.2 Hz, 1H, 4-H(F)$_{ax}$), 2.89 (dd, J=5.1, 16.2 Hz, 1H, 4-H(F)$_{eq}$), 3.49–3.82 (7×s, 21H, 7×OCH$_3$), 3.92–3.94 [m, 1H, 3-H(F)], 4.06 [dd, J=6.4, 9.2 Hz, 1H, 3-H(C)], 4.33 [br s, 1H, 2-H(F)], 4.89 [d, 1H, J=6.4 Hz, 4-H(C)], 4.98 [d, 1H, J=9.2 Hz, H-2(C)], 5.75 [br s, 1H, 6-H(D)], 6.00 [br s, 1H, 6/8-H(A)], 6.30 [br s, 1H, 6/8-H(A)], 6.80-6.96 [m, 6H, 2,5,6-H(E)/(D)]. $^{13}$C NMR: δ (DMSO) 29.0 (C-4(F)), 32.6 (C-4(C)), 41.1 (1×OCH$_3$), 55.5–57.1 (7×OCH$_3$), 67.2 (C-3(F)), 70.7 (C-3(C)), 78.3 (C-2(C)), 79.1 (C-6/8(A)), 79.3 (C-6/8(A)), 79.5, 82.2, 91.9, 92.5, 94.1, 107.0, 110.4, 113.2, 113.4, 113.5, 113.8, 120.6, 121.1, 133.0, 133.9, 149.6, 154.3, 156.3, 157.0, 158.6, 158.7, 159.6. CD: □ nm (θ), 205.50 (−1.924×10$^2$), 212.00 (1.204×10$^3$), 221.00 (−1.051×10$^3$), 227.50 (6.870×10$^1$), 233.00 (−1.796×10$^3$), 242.5.80 (2.583×10$^4$), 277.00 (3.277×10$^3$).

Compound 21:
Found M$^+$ 774.28859, C$_{38}$H$_{42}$O$_{12}$ requires M$^+$ 774.28876, M$^+$ 774 (78) m/e 714 (100), 654 (31), 511 (35), 345 (18). IR: $\overline{v}_{max}$ 2927, 2837, 1700, 1595, 1518 cm$^{-1}$. $^1$H NMR: δ (CDCl$_3$, 25° C.) 1.72 and 1.80 (2×s, 2×3H, 2×COCH$_3$), 1.83 and 1.99 (2×s, 2×3H, 2×COCH$_{3 rot.}$), 2.60 (dd, J=8.8, 16.5 Hz, 1H, 4-H(F)$_{ax}$), 2.70 (dd, J=5.2, 17.6 Hz, 1H, 4-H(F)$_{ax\ rot.}$), 2.82 (dd, J=2.6, 17.6 Hz, 1H, 4-H(F)$_{eq}$ 3.16 (dd, J=6.5, 16.5 Hz, 1H, 4-H(F)$_{eq}$), 3.33–3.87 (15×s, 48H, 16×OCH$_3$), 4.08 [d, J=8.9 Hz, 1H, 2-H(F)], 5.01 [d, 1H, J=6.3 Hz, 4-H(C)], 5.14 (d, 1H, J=6.0 Hz, 4-H(C)$_{rot.}$), 5.14–5.18 [m, 1H, 3-H(F)], 5.20 (d, J=3.6 Hz, 1H, 2-H(F)$_{rot.}$), 5.25 (d, 1H, J=10.4 Hz, 2-H(C)$_{rot.}$), 5.30 [d, J=2.4 Hz, 1H, 6/8-H(A)], 5.31 [d, 1H, J=10.4 Hz, 2-H(C)], 5.32-5.34 (m, 1H, 3-H(F)$_{rot.}$), 5.46 [dd, J=6.3, 10.4 Hz, 1H, 3-H(C)], 5.50 (dd, J=6.0, 10.4 Hz, 1H, 3-H(C)$_{rot.}$), 5.84 [d, J=2.4 Hz, 1H, 6/8-H(A)], 6.03 (d, J=2.3 Hz, 1H, 6/8-H(A)$_{rot.}$), 6.11 (s, 1H, 6-H(D)$_{rot.}$), 6.18 (d, J=2.3 Hz, 1H, 6/8-H(A)$_{rot.}$), 6.19 [s, 1H, 6-H(D)], 6.63 [dd, J=2.0, 8.2 Hz, 1H, 6-H(E)], 6.68 [d, J=2.0 Hz, 1H, 2-H(E)], 6.72 [d, J=8.2 Hz, 1H, 5-H(E)], 6.80 [dd, J=1.8, 8.3 Hz, 1H, 6-H(B)], 6.81 (d, J=8.3 Hz, 1H, 5-H(B)$_{rot.}$), 6.82 (d, J=8.3 Hz, 1H, 5-H(E)$_{rot.}$), 6.86 [d, J=1.8 Hz, 1H, 2-H(B)], 6.87 (d, J=1.8 Hz, 1H, 2-H(E)$_{rot.}$), 6.92 (dd, J=1.8, 8.3 Hz, 1H, 6-H(B)$_{rot.}$), 6.93 (d, J=1.8 Hz, 1H, 2-H(B)$_{rot.}$), 6.96 [d, J=8.3 Hz, 1H, 5-H(B)], 6.97 (dd, J=1.8, 8.3 Hz, 1H, 6-H(E)$_{rot.}$). $^{13}$C NMR: δ (CDCl$_3$, 25° C.) 20.8-21.3 (2×COCH$_3$ and 2×COCH$_{3 rot.}$), 21.9 (C-4 (F)$_{rot.}$), 26.7 (C-4(F)), 26.7, 30.3 (C-4(C)$_{rot.}$), 30.4 (C-4(C)), 54.8–56.6 (8×OCH$_3$ and 8×OCH$_{3 rot.}$), 69.2 (C-3(F)$_{rot.}$), 69.9 (C-3(F)), 71.8 (C-3(C)), 72.1 (C-3(C)$_{rot.}$), 75.5 (C-2(C)), 75.9 (C-2(C)$_{rot.}$), 77.9 (C-2(F)$_{rot.}$), 79.3 (C-2(F)), 88.7 (C-6(D)$_{rot.}$), 91.0 (C-6(D)), 91.5 (C-6/8(A)$_{rot.}$), 91.6 (C-6/8 (A)), 92.0 (C-6/8(A)), 92.7 (C-6/8(A)$_{rot.}$), 100.2, 103.0, 104.8, 105.3, 109.0, 109.2, 109.5 (C-2(B)), 110.0 (C-2(E)), 110.4 (C-5(E)), 110.7 (C-2(E)$_{rot.}$), 110.7, 110.8 (C-6(B)), 111.1, 118.1, 119.6 (C-6(E)), 120.4 (C-6(B)rot.), 120.4 (C-6 (E)$_{rot.}$), 129.8, 131.1, 131.2, 131.2, 148.3 (C—OCH$_3$), 148.6, 148.7 (2×C—OCH$_3$), 148.7, 148.9 (3×s), 152.9, 154.4, 155.8, 156.4, 156.8, 157.0, 157 7, 158.1, 158.3, 158.7, 159.1, 159.6, 169.3-170.3 (4×COCH$_3$). CD: □ nm (θ), 213.50 (−3.878×10$^1$), 221.00 (2.202×10$^2$), 230.50 (−4.873×10$^2$), 248.00 (7.377×10$^3$), 288.00 (−7.828×10$^3$), 330.00 (2.544×10$^1$).

It will be appreciated from the foregoing that the starting material for the method according to the invention comprises the 3-oxo-derivative, which contains only an electrophilic centre and a second compound that only comprises a nucleophilic centre. After C—C bond formation and reduction of Formula (IV) in accordance with the method of the invention, the resultant dimer product cannot react any further, unless the 3-hydroxy group of the flavanol species coupled to the 3-oxo-derivative is oxidised to a 3-oxo group thereby activating the C-4 position and allowing for further controlled polymerisation.

The invention claimed is:

1. A method of introducing a nucleophilic aromatic moiety onto an unsubstituted C-4 carbon of a compound having a flavan-3-ol structure, comprising the steps of
   (a) converting the hydroxy group of the compound having the flavan-3-ol structure to an oxo group to form a flavan-3-one of that compound;
   (b) contacting the flavan-3-one of that compound with a compound containing the nucleophilic aromatic moiety in the presence of an oxidising agent;
   (c) allowing a carbon to carbon bond to form between the C-4 carbon of the flavan-3-one compound and a carbon of the nucleophilic aromatic moiety; and
   (d) reducing the flavan-3-one moiety to obtain the corresponding flavan-3-ol compound which is substituted by the nucleophilic moiety on the C-4 carbon.

2. A method of preparing a flavonoid having substituents on its C-3 and C-4 carbons in 3,4-cis configuration, comprising the steps of
   (a) providing a compound having a flavan-3-ol structure and which is unsubstituted on the C-4 carbon;
   (b) providing a compound having a nucleophilic aromatic moiety;
   (c) converting the hydroxy group of the compound having the flavan-3-ol structure to an oxo group to form a flavan-3-one of that compound;
   (d) contacting the flavan-3-one of that compound with a compound containing the nucleophilic aromatic moiety in the presence of an oxidising agent;
   (e) allowing a carbon to carbon bond to form between the C-4 carbon of the flavan-3-one compound and a carbon of the nucleophilic aromatic moiety;
   (f) reducing the flavan-3-one moiety to obtain the corresponding flavan-3-ol compound which is substituted by the nucleophilic aromatic moiety on the C-4 carbon in a mixture of the 3,4-cis and 3,4-trans configurations of that compound; and
   (g) separating the 3,4-cis and 3,4-trans configurations of the compound.

3. A method according to claim 1 for the preparation of proanthocyanidins and proanthocyanidin analogues, the method comprising the steps of
   (a) providing a 3-oxo-derivative of a flavan-3-ol, represented by Formula (I) (hereinafter referred to as "the 3-oxo-derivative"):

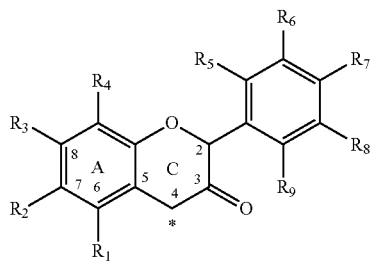

Formula (I)

wherein
each of $R_1$, $R_2$, $R_3$, $R_4$, $R_5$, $R_6$, $R_7$, $R_8$ and $R_9$ is independently selected from the group consisting of —H, —OH, hydrocarbyl groups, saccharide moieties and —$OR_{10}$;
wherein $R_{10}$ is selected from the group consisting of a hydrocarbyl group, an acyl group and a benzyl group; and
wherein the hydrocarbyl groups in any one of $R_1$ to $R_{10}$ and the acyl group contains from 1 to 10 carbon atoms;
   (b) providing an additional compound which is to constitute at least part of the proanthocyanidin or proanthocyanidin analogue, and which additional compound has a nucleophilic aromatic moiety (hereinafter referred to as "the additional compound");
   (c) protecting each phenolic and each saccharide hydroxy group of the 3-oxo-derivative and of the additional compound to form a protected 3-oxo-derivative and protected additional compounds;
   (d) contacting the protected 3-oxo-derivative or the 3-oxo-derivative without any phenolic hydroxy groups or saccharide hydroxy groups with the protected additional compound or additional compound without any phenolic or saccharide hydroxy group in the presence of an oxidising agent;
   (e) allowing a direct C—C bond to form between with the carbon atom in the 4-position of the 3-oxo-derivative (shown by "*" in Formula (I)) and a carbon atom which is part of the nucleophilic aromatic moiety of the additional compound;
   (f) optionally, and where the additional compound has a flavonoid base structure having no substituent at its C-4 position and a hydroxy group at its C-3 position, oxidizing the hydroxide group to provide a secondary 3-oxo-derivative;
   (g) and further optionally providing a secondary additional compound which is to constitute at least part of the proanthocyanidin or proanthocyanidin analogue, and which secondary additional compound has a nucleophilic aromatic moiety (hereinafter referred to as "the secondary additional compound"); and
   (h) contacting the secondary 3-oxo-derivative with the secondary additional compound in the presence of an oxidising agent.

4. The method of claim 3 wherein $R_1$-$R_{10}$ are linear hydrocarbyl groups or cyclic hydrocarbyl groups.

5. The method of claim 3 wherein $R_{10}$ is a benzyl group or an acyl group.

6. The method of claim 3 wherein $R_1$-$R_9$ is independently a saccharide moiety.

7. The method of claim 1 wherein the compound having a nucleophilic aromatic moiety is selected from the group consisting of compounds having a phenolic, flavanyl or flavonoid moiety.

8. The method of claim 1 wherein the compound having a nucleophilic aromatic moiety is a compound having a protected phenolic moiety.

9. The method of claim 1 wherein the compound having a nucleophilic aromatic moiety is a compound having a protected flavanyl or flavonoid moiety.

10. The method of claim 1 wherein the oxidising agent is selected from the group consisting of $AgBF_4$, $Pb(OAc)_4$, DDQ, $OsO_4$, Tollens reagent, $KMnO_4$, and pyridinium chlorochromate.

11. The method of claim 10 wherein the oxidising agent is $AgBF_4$.

12. The method of claim 1 wherein the compound having a nucleophilic aromatic moiety, the 3-oxo-derivative and the oxidising agent are mixed together in the presence of a solvent selected from the group consisting of tetrahydrofuran, diethyl ether and any aprotic solvent that is capable of dissolving said compound and the 3-oxo-derivative.

13. A method of preparing a mixture of flavonoid compounds having substituents on their C-3 and C-4 carbons, comprising the steps of
(a) providing a compound having a flavan-3-ol structure and which is unsubstituted on the C-4 carbon;
(b) providing a compound having a nucleophilic aromatic moiety;
(c) converting the hydroxy group of the compound having the flavan-3-ol structure to an oxo group to form a flavan-3-one of that compound;
(d) contacting the flavan-3-one of that compound with a compound containing the nucleophilic aromatic moiety in the presence of an oxidising agent;
(e) allowing a carbon to carbon bond to form between the C-4 carbon of the flavan-3-one compound and a carbon of the nucleophilic aromatic moiety; and
(f) reducing the flavan-3-one moiety to obtain the corresponding flavan-3-ol compound which is substituted by the nucleophilic aromatic moiety on the C-4 carbon in a mixture of the 3,4-cis and 3,4-trans configurations of that compound.

14. A method according to claim 2 for the preparation of proanthocyanidins and proanthocyanidin analogues, the method comprising the steps of
(a) providing a 3-oxo-derivative of a flavan-3-ol, represented by Formula (I) (hereinafter referred to as "the 3-oxo-derivative"):

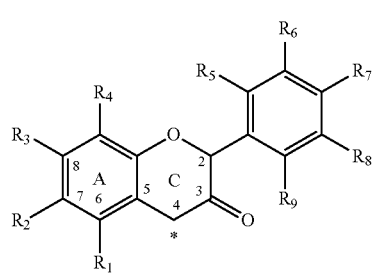

Formula (I)

wherein
each of $R_1$, $R_2$, $R_3$, $R_4$, $R_5$, $R_6$, $R_7$, $R_8$ and $R_9$ is independently selected from the group consisting of —H, —OH, hydrocarbyl groups, saccharide moieties and —$OR_{10}$;
wherein $R_{10}$ is selected from the group consisting of a hydrocarbyl group, an acyl group and a benzyl group; and wherein the hydrocarbyl groups in any one of $R_1$ to $R_{10}$ and the acyl group contains from 1 to 10 carbon atoms;
(b) providing an additional compound which is to constitute at least part of the proanthocyanidin or proanthocyanidin analogue, and which additional compound has a nucleophilic aromatic moiety (hereinafter referred to as "the additional compound");
(c) protecting each phenolic and each saccharide hydroxy group of the 3-oxo-derivative and of the additional compound to form a protected 3-oxo-derivative and protected additional compounds;
(d) contacting the protected 3-oxo-derivative or the 3-oxo-derivative without any phenolic hydroxy groups or saccharide hydroxy groups with the protected additional compound or additional compound without any phenolic or saccharide hydroxy group in the presence of an oxidising agent;
(e) allowing a direct C—C bond to form between with the carbon atom in the 4-position of the 3-oxo-derivative (shown by "*" in Formula (I)) and a carbon atom which is part of the nucleophilic aromatic moiety of the additional compound;
(f) optionally, and where the additional compound has a flavonoid base structure having no substituent at its C-4 position and a hydroxy group at its C-3 position, oxidizing the hydroxide group to provide a secondary 3-oxo-derivative;
(g) and further optionally providing a secondary additional compound which is to constitute at least part of the proanthocyanidin or proanthocyanidin analogue, and which secondary additional compound has a nucleophilic aromatic moiety (hereinafter referred to as "the secondary additional compound"); and
(h) contacting the secondary 3-oxo-derivative with the secondary additional compound in the presence of an oxidising agent.

15. The method of claim 2 wherein the compound having a nucleophilic aromatic moiety is selected from the group consisting of compounds having a phenolic, flavanyl or flavonoid moiety.

16. The method of claim 2 wherein the compound having a nucleophilic aromatic moiety is a compound having a protected phenolic moiety.

17. The method of claim 2 wherein the compound having a nucleophilic aromatic moiety is a compound having a protected flavanyl or flavonoid moiety.

18. The method of claim 2 wherein the oxidising agent is selected from the group consisting of $AgBF_4$, $Pb(OAc)_4$, DDQ, $OsO_4$, Tollens reagent, $KMnO_4$, and pyridinium chlorochromate.

19. The method of claim 2 wherein the compound having a nucleophilic aromatic moiety, the 3-oxo-derivative and the oxidising agent are mixed together in the presence of a solvent selected from the group consisting of tetrahydrofuran, diethyl ether and any aprotic solvent that is capable of dissolving said compound and the 3-oxo-derivative.

20. The method of claim 14 wherein $R_1$-$R_{10}$ are linear hydrocarbyl groups or cyclic hydrocarbyl groups.

21. The method of claim 14 wherein $R_{10}$ is a benzyl group or an acyl group.

22. The method of claim 14 wherein $R_1$-$R_9$ is independently a saccharide moiety.

23. The method of claim 18 wherein the oxidising agent is $AgBF_4$.

24. The method of claim 3, further comprising step (i): repeating the steps (f), (g) and (h) as many times as is necessary to achieve the incorporation of the desired number of monomeric units in the resultant proanthocyanidin or proanthocyanidin analogue.

25. The method of claim 3, further comprising step (j): reducing the resulting proanthocyanidin or proanthocyanidin analogue to convert the oxo group on the various C-3 positions of the respective 3-oxo-derivative units introduced into the resultant products to a hydroxide group.

26. The method of claim 3, further comprising step (k): removing any or all of the phenolic or saccharide hydroxy protecting groups to yield the unprotected hydroxy compounds.

27. The method of claim 4, wherein $R_1$-$R_{10}$ are selected from methyl, ethyl, propyl, butyl, pentyl, hexyl, heptyl, octyl, nonyl, decyl, cyclopropyl, cyclobutytl, cyclopentytl, cyclohexyl, cycloheptyl, cyclooctyl, cyclononyl, and cyclodecyl.

28. The method of claim 6, wherein the saccharide moiety is selected from monosaccharides, disaccharides, oligosaccharides, polysaccharides, and analogues of these saccharides.

29. The method of claim 1, wherein the compound having a nucleophilic aromatic moiety is 1,3,5 tri-methoxybenzene.

30. The method of claim 1, wherein the compound having a nucleophilic aromatic moiety is 5,7,3',4'-tetra-O-methylcatechin.

31. The method of claim 14, further comprising step (i), repeating the steps (f), (g) and (h) as many times as is necessary to achieve the incorporation of the desired number of monomeric units in the resultant proanthocyanidin or proanthocyanidin analogue.

32. The method of claim 14, further comprising step (j): reducing the resulting proanthocyanidin or proanthocyanidin analogue to convert the oxo group on the various C-3 positions of the respective 3-oxo-derivative units introduced into the resultant products to a hydroxide group.

33. The method of claim 14, further comprising step (k): removing any or all of the phenolic or saccharide hydroxy protecting groups to yield the unprotected hydroxy compounds.

34. The method of claim 14, wherein the compound having a nucleophilic aromatic moiety is 1,3,5 tri-methoxybenzene.

35. The method of claim 14, wherein the compound having a nucleophilic aromatic moiety is 5,7,3'4-tetra-O-methylcatechin.

36. The method of claim 20, wherein $R_1$-$R_{10}$ are selected from methyl, ethyl, propyl, butyl, pentyl, hexyl, heptyl, octyl, nonyl, decyl, cyclopropyl, cyclobutytl, cyclopentytl, cyclohexyl, cycloheptyl, cyclooctyl, cyclononyl, and cyclodecyl.

37. The method of claim 22, wherein the saccharide moiety is selected from monosaccharides, disaccharides, oligosaccharides, polysaccharides, and analogues of these saccharides.

* * * * *

UNITED STATES PATENT AND TRADEMARK OFFICE
CERTIFICATE OF CORRECTION

PATENT NO. : 8,501,970 B2  
APPLICATION NO. : 12/995379  
DATED : August 6, 2013  
INVENTOR(S) : Jan H. Van Der Westhuizen et al.

Page 1 of 1

It is certified that error appears in the above-identified patent and that said Letters Patent is hereby corrected as shown below:

In the Specification

Column 10,
line 39, "δ8.1 (C-4)," should read --38.1 (C-4),--.

Column 14,
line 51, "3"15"-H)," should read --3"/5"-H),--.

Column 16,
Line 37, "NMR: (CDCl$_3$)" should read --NMR: δ (CDCl$_3$)--.
Line 46, "NMR: 5" should read --NMR: δ--.

Column 18,
Line 37, "4-H(F)$_{eq}$" should read --4-H(F)$_{eq\ rot.}$),--.

Signed and Sealed this
Fourth Day of November, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,501,970 B2                                    Page 1 of 1
APPLICATION NO.  : 12/995379
DATED            : August 6, 2013
INVENTOR(S)      : Van Der Westhuizen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 194 days.

Signed and Sealed this

Fifteenth Day of September, 2015

Michelle K. Lee
*Director of the United States Patent and Trademark Office*